US006968230B2

(12) United States Patent
Waltman

(10) Patent No.: US 6,968,230 B2
(45) Date of Patent: Nov. 22, 2005

(54) H-BRIDGE CIRCUIT FOR GENERATING A HIGH-ENERGY BIPHASIC AND EXTERNAL PACING WAVEFORM IN AN EXTERNAL DEFIBRILLATOR

(75) Inventor: Barry F. Waltman, Brier, WA (US)

(73) Assignee: Medtronic Physio-Control Manufacturing Corp, Redmond, WA (US)

( * ) Notice: Subject to any disclaimer, the term of this patent is extended or adjusted under 35 U.S.C. 154(b) by 420 days.

(21) Appl. No.: 10/186,248

(22) Filed: Jun. 26, 2002

(65) Prior Publication Data

US 2004/0002736 A1 Jan. 1, 2004

(51) Int. Cl.[7] ................................................. A61N 1/39
(52) U.S. Cl. .......................................................... 607/4
(58) Field of Search ........................................ 607/4–9

(56) References Cited

U.S. PATENT DOCUMENTS

| | | |
|---|---|---|
| 1,662,771 A | 3/1928 | Whittingham |
| 1,840,168 A | 1/1932 | Mucher |
| 1,841,332 A | 1/1932 | Kranz |
| 2,298,315 A | 10/1942 | Siegel et al. |
| 2,464,820 A | 3/1949 | Livera |
| 4,038,628 A | 7/1977 | Salemi |
| 4,274,136 A | 6/1981 | Onodera et al. |
| 4,402,322 A | 9/1983 | Duggan |
| 4,693,253 A | 9/1987 | Adams |
| 4,800,883 A | 1/1989 | Winstrom |
| 4,821,723 A | 4/1989 | Baker, Jr. et al. |
| 4,850,357 A | 7/1989 | Bach, Jr. |
| 5,048,521 A | 9/1991 | Pless et al. |
| 5,083,562 A | 1/1992 | de Coriolis et al. |
| 5,099,844 A | 3/1992 | Faupel |
| 5,358,512 A | 10/1994 | Hoegnelid et al. |
| 5,376,103 A | 12/1994 | Anderson et al. |
| 5,431,682 A | 7/1995 | Hedberg |
| 5,431,684 A | 7/1995 | Archer et al. |
| 5,431,686 A | 7/1995 | Kroll et al. |
| 5,441,518 A | 8/1995 | Adams et al. |

(Continued)

FOREIGN PATENT DOCUMENTS

EP           0 315 768         5/1989

(Continued)

OTHER PUBLICATIONS

"Defibrillator," a Russian defibrillator manual (in English), 1993.

(Continued)

Primary Examiner—Scott M. Getzow

(57) ABSTRACT

A circuit for generating both a biphasic defibrillation waveform and an external pacing waveform in an external defibrillator is provided. The output circuit of the device utilizes one or more SCR switches for applying energy to a patient. In one embodiment, the output circuit is in the form of an H-bridge, with three SCR legs and one IGBT leg. A drive circuit for one of the SCR legs is provided such that the SCR may be continuously driven on for either a high energy biphasic defibrillation pulse or a low energy pacing pulse. In one embodiment, the output circuit conducts the pacing waveform through a combination of one upper leg SCR of the H-bridge and a current source. The current source is configured to bypass a lower leg SCR of the H-bridge. The output circuit is capable of conducting pacing currents of as low as 10 mA. The output circuit is also capable of conducting a high energy biphasic defibrillation waveform of as high as 200 or more joules, and also a low energy defibrillation pulse of as low as 1 to 50 joules. The output circuit is also capable of conducting currents as high as approximately 200 amperes.

29 Claims, 4 Drawing Sheets

U.S. PATENT DOCUMENTS

| | | | |
|---|---|---|---|
| 5,468,254 A | 11/1995 | Hahn et al. | |
| 5,470,341 A | 11/1995 | Kuehn et al. | |
| 5,489,293 A | 2/1996 | Pless et al. | |
| 5,507,781 A | 4/1996 | Kroll et al. | |
| 5,514,160 A | 5/1996 | Kroll et al. | |
| 5,522,853 A | 6/1996 | Kroll | |
| 5,531,765 A | 7/1996 | Pless | |
| 5,534,015 A | 7/1996 | Kroll et al. | |
| 5,591,209 A | 1/1997 | Kroll | |
| 5,591,210 A | 1/1997 | Kroll et al. | |
| 5,591,211 A | 1/1997 | Meltzer | |
| 5,591,213 A | 1/1997 | Morgan | |
| 5,593,427 A | 1/1997 | Gliner et al. | |
| 5,601,608 A | 2/1997 | Mouchawar | |
| 5,601,612 A | 2/1997 | Gliner et al. | |
| 5,607,454 A | 3/1997 | Cameron et al. | |
| 5,620,465 A | 4/1997 | Olson et al. | |
| 5,674,266 A | 10/1997 | Stendahl | |
| 5,733,310 A | 3/1998 | Lopin et al. | |
| 5,824,017 A | 10/1998 | Sullivan et al. | |
| 5,873,893 A | 2/1999 | Sullivan et al. | |
| 5,879,374 A | 3/1999 | Powers et al. | |
| 6,041,254 A | 3/2000 | Sullivan et al. | |
| 6,104,953 A * | 8/2000 | Leyde | 607/4 |
| 6,175,765 B1 | 1/2001 | Sullivan et al. | |
| 6,208,895 B1 | 3/2001 | Sullivan et al. | |
| 6,477,413 B1 | 11/2002 | Sullivan et al. | |

FOREIGN PATENT DOCUMENTS

| | | |
|---|---|---|
| EP | 0 315 768 A2 | 5/1989 |
| EP | 0 553 864 A2 | 8/1993 |
| EP | 0 747 093 A2 | 12/1996 |
| WO | WO 93/16759 | 9/1993 |
| WO | WO 94/27674 | 12/1994 |
| WO | WO 95/05215 | 2/1995 |
| WO | WO 95/09673 | 4/1995 |
| WO | WO 98/39060 | 9/1998 |
| WO | WO 98/39061 | 9/1998 |

OTHER PUBLICATIONS

"Portable Defibrillator With General-Purpose Power Supply," an advertising brochure for a Russian defibrillator (in Russian and English), 1994, 4 pages.

G.H. Bardy et al., "Multicenter Comparison of Truncated Biphasic Shocks and Standard Damped Sine Wave Monophasic Shocks for Transthoracic Ventricular Defibrillation," *Circulation* 94(10):2507-2514, Nov. 15, 1996.

G.H. Bardy et al., "Truncated Biphasic Pulses for Transthoracic Defibrillation," *Circulation* 91(6):1768-1774, Mar. 15, 1995.

R.O. Cummins et al., Overview, "Ventricular Fibrillation, Automatic External Defibrillators, and the United States Food and Drug Administration: Confrontation Without Comprehension," *Annals of Emergency Medicine* 26(5): 621-631, Nov. 1995.

S.A. Feeser et al., Abstract, "Strength-Duration and Probability of Success Curves for Defibrillation With Biphasic Waveforms," *Circulation* 82:2128, 1990.

B.E. Gliner et al., "Transthoracic Defibrillation of Swine with Monophasic and Biphasic Waveforms," *Circulation* 92(6):1634-1643, Sep. 15, 1995.

Kroll, M.W., "A Minimal Model of the Single Capacitor Biphasic Defibrillation Waveform," *PACE* 17(1):1782-1792, Nov. 1994.

A.S.L. Tang et al., Abstract, "Ventricular Defibrillation Using Biphasic Waveforms: The Importance of Phasic Duration," *Journal of American College of Cardiology* 13(1): 207, Jan. 1989.

G.P. Walcott et al., "Choosing the Optimal Monophasic and Biphasic Waveforms for Ventricular Defibrillation," *Journal of Cardiovascular Electrophysiology* 6(9):737-750, Sep. 1995.

* cited by examiner

H-BRIDGE CIRCUIT FOR GENERATING A HIGH-ENERGY BIPHASIC AND EXTERNAL PACING WAVEFORM IN AN EXTERNAL DEFIBRILLATOR

FIELD OF THE INVENTION

This invention relates generally to apparatus for generating defibrillation and pacing waveforms, and more particularly to a circuit for generating a high-energy biphasic and external pacing waveform in an external defibrillator.

BACKGROUND OF THE INVENTION

One of the most common and life-threatening medical conditions is ventricular fibrillation, a condition where the human heart is unable to pump the volume of blood required by the human body. The generally accepted technique for restoring a normal rhythm to a heart experiencing ventricular fibrillation is to apply a strong electric pulse to the heart using an external cardiac defibrillator. External cardiac defibrillators have been successfully used for many years in hospitals by doctors and nurses, and in the field by emergency treatment personnel, e.g., paramedics.

Conventional external cardiac defibrillators first accumulate a high-energy electric charge on an energy storage capacitor. When a switching mechanism is closed, the stored energy is transferred to a patient in the form of a large current pulse. The current pulse is applied to the patient via a pair of electrodes positioned on the patient's chest. The switching mechanism used in most contemporary external defibrillators is a high-energy transfer relay. A discharge control signal causes the relay to complete an electrical circuit between the storage capacitor and a wave shaping circuit whose output is connected to the electrodes attached to the patient.

The relay used in contemporary external defibrillators has traditionally allowed a monophasic waveform to be applied to the patient. It has recently been discovered, however, that there may be certain advantages to applying a biphasic rather than a monophasic waveform to the patient. For example, preliminary research indicates that a biphasic waveform may limit the resulting heart trauma associated with the defibrillation pulse.

The American Heart Association has recommended a range of energy levels for the first three defibrillation pulses applied by an external defibrillator. The recommended energy levels are: 200 joules for a first defibrillation pulse; 200 or 300 joules for a second defibrillation pulse; and 360 joules for a third defibrillation pulse, all within a recommended variance range of no more than plus or minus 15 percent according to standards promulgated by the Association for the Advancement of Medical Instrumentation (AAMI). These high energy defibrillation pulses are required to ensure that a sufficient amount of the defibrillation pulse energy reaches the heart of the patient and is not dissipated in the chest wall of the patient.

On the other hand, pacers are typically used to administer a series of relatively small electrical pulses to a patient experiencing an irregular heart rhythm. For example, each pacing pulse typically has an energy of about 0.05 J to 1.2 J. Because of the small energies used for pacing pulses, the circuitry used to generate the pacing pulses cannot typically be used for generating defibrillation pulses, which are typically of much higher energies and currents.

There are some systems that combine both a pacer and a defibrillator in a single unit for providing pacing pulses and defibrillation pulses as required. These conventional systems typically use separate defibrillation and pacing generation circuits. Implantable systems generally use separate electrodes for pacing and defibrillation. An example of an implantable combined defibrillator/pacer is found in U.S. Pat. No. 5,048,521. Of course, having separate defibrillation and pacing circuits tends to increase the cost and size of the unit. In addition, because implantable defibrillators and pacers typically apply relatively low energy pulses, the output circuitry for such implantable units is generally not adaptable for use in an external unit.

The present invention is directed to an apparatus that overcomes the foregoing and other disadvantages in an external pacing/defibrillation unit. More specifically, the present invention is directed to a single output circuit for an external pacer/defibrillator that utilizes switches for applying both high-energy biphasic defibrillation pulses and low-energy pacing pulses to a patient.

SUMMARY OF THE INVENTION

In accordance with the present invention, an external defibrillator/pacer having an output circuit that is used in generating both a defibrillation pulse and a pacing pulse is provided. The output circuit includes four legs arrayed in the form of an "H" (hereinafter the "H-bridge output circuit"). Each leg of the output circuit contains a solid-state switch. By selectively switching on pairs of switches in the H-bridge output circuit, biphasic or monophasic defibrillation and pacing pulses may be applied to a patient.

In accordance with one aspect of the invention, the switches in one or more of the legs of the H-bridge output circuit are silicon controlled rectifiers (SCRs). A single SCR may be used in each leg. The switches in one or more of the other legs may be insulated gate bipolar transistors (IGBTs). In one embodiment, the output circuit is formed with three SCR legs and one IGBT leg.

In accordance with another aspect of the invention, the pacing current is conducted through one of the SCRs of the H-bridge. A drive circuit for the SCR is derived such that the SCR may be continuously driven on for either a biphasic waveform pulse or a pace waveform pulse. The drive circuit is able to hold on the high power SCR at current levels well below the holding current levels of the SCR, such as may occur during pacing applications. Additionally, for delivering the high energy biphasic defibrillation waveform, the drive circuit has sufficient drive level to turn on the high power SCR for delivering the high energy defibrillation waveform. This topology is advantageous in that a single power switch can be utilized for generating the pace waveform pulse or the biphasic waveform pulse, thus reducing the total number of parts required to implement both biphasic and pacing waveform generation.

In accordance with yet another aspect of the invention, the H-bridge output circuit conducts the pacing waveform through a combination of one upper leg SCR of the H-bridge and a current source. The current source is configured to essentially bypass one of the lower leg SCRs of the H-bridge.

In accordance with still another aspect of the invention, a single power switch is utilized in each of the legs of the H-bridge output circuit, and are included in a single integrated module or package. The use of single semiconductor switches in an integrated surface mountable module or package simplifies the assembly and manufacturing of the defibrillator device. The use of a single IGBT in a leg of the H-bridge (as opposed to two or more IGBTs in series) also greatly simplifies the drive circuitry required to turn on and off the IGBT.

In accordance with yet another aspect of the invention, the H-bridge output circuit is capable of conducting a high-energy biphasic waveform of 200 or more joules from the energy storage capacitor to the patient. In addition, the H-bridge output circuit is capable of conducting a low energy defibrillation pulse as low as 1 to 50 joules.

In accordance with still another aspect of the invention, a gate drive circuit biases the IGBT in the fourth leg of the H-bridge on with sufficient voltage over a short interval to conduct upwards to 200 amperes of current. This gate drive circuit is greatly simplified in that the drive circuit has to drive only one IGBT device. In general, all of the output circuit power switches are selected to have sufficient current conducting capability to allow switches in two legs of the H-bridge to provide a shorting path for discharging unwanted energy from the energy storage capacitor.

In accordance with yet another aspect of the invention, a resistive component of the H-bridge is incorporated into a protective component that limits both current and voltage changes from the energy storage capacitor.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
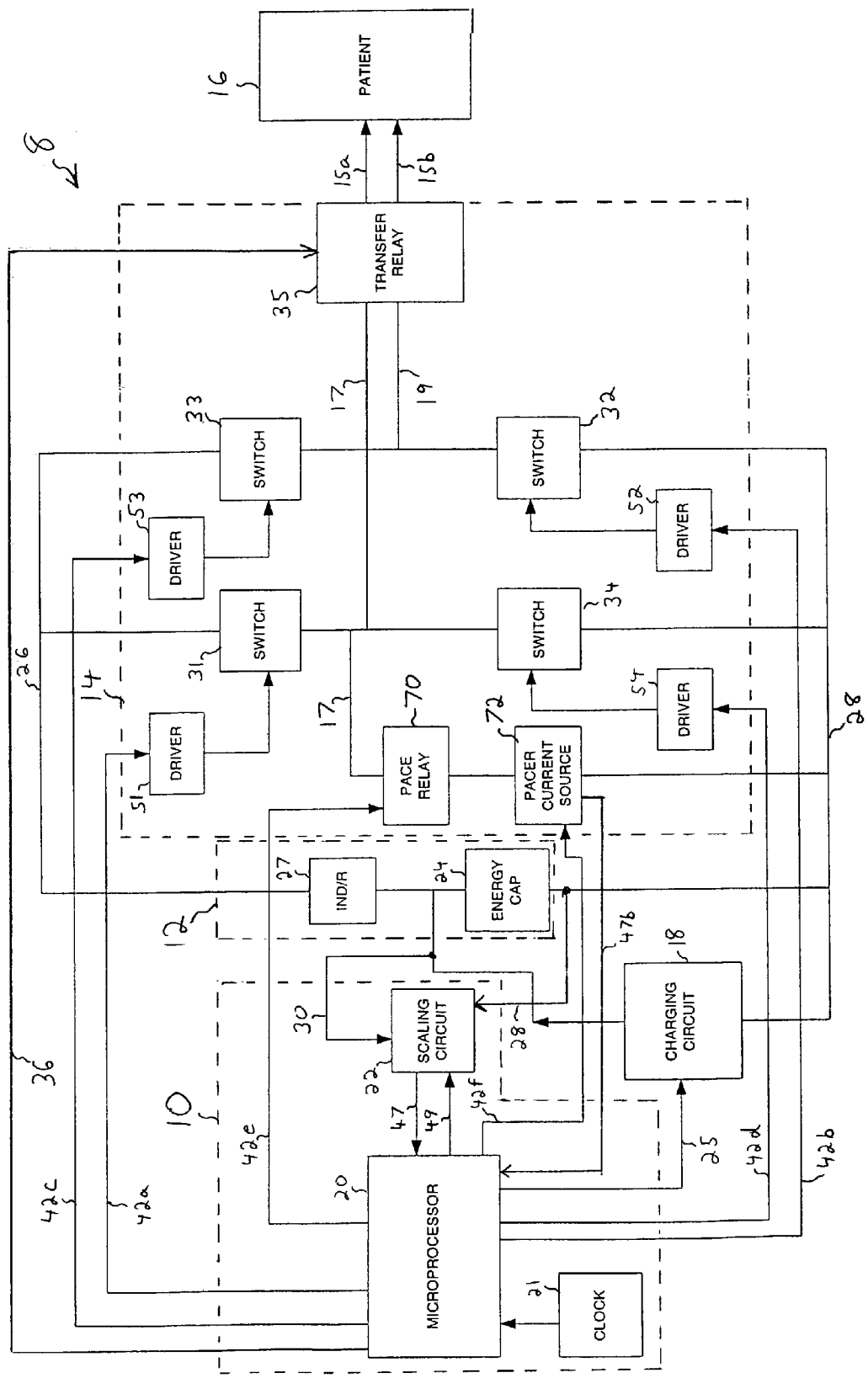
FIG. 1 is a block diagram illustrative of a combined defibrillator/pacer unit having a single output circuit, in accordance with the present invention.

FIG. 1 is a block diagram illustrative of an external combined defibrillator/pacer 8, according to one embodiment of the present invention. The defibrillator/pacer 8 is connected to a patient 16 and includes a microprocessor 20 that is connected to an energy storage capacitor 24 via a charging circuit 18. It will be appreciated by those skilled in the art that energy storage capacitor 24 may be implemented with a multi-capacitor network (i.e., with capacitors connected in series and/or parallel). During the operation of the defibrillator/pacer 8, microprocessor 20 controls charging circuit 18 using a signal on a control line 25 to charge energy storage capacitor 24 to a desired voltage level. To monitor the charging process, microprocessor 20 is connected to a scaling circuit 22 by a measurement line 47, and by a control line 49. It will be understood that while single measurement and control lines are shown, multiple lines may be used. Scaling circuit 22 is connected to energy storage capacitor 24 by a bridge line 28, which connects to the negative lead of energy storage capacitor 24, and by a line 30, which connects to the positive lead of the capacitor. A clock 21 is also connected to microprocessor 20.

Scaling circuit 22 is used to step down the voltage across energy storage capacitor 24 to a range that may be monitored by microprocessor 20. Scaling circuit 22 is described briefly below and in more detail in U.S. Pat. No. 5,873,893, entitled "Method and Apparatus for Verifying the Integrity of an Output Circuit Before and During Application of A Defibrillation Pulse," which is commonly assigned and hereby incorporated by reference in its entirety. Energy storage capacitor 24 can be charged to a range of voltage levels, with the selected level depending on the patient and other parameters. Preferably, the size of energy storage capacitor 24 falls within a range from 150 $\mu$F to 200 $\mu$F. In order to generate the necessary defibrillation pulse for external application to a patient, energy storage capacitor 24 is charged to between 100 volts and 2,200 volts. To detect small percentage changes in the selected voltage level of energy storage capacitor 24, scaling circuit 22 is adjustable to measure different voltage ranges. The adjusted output is measured by microprocessor 20 on measurement line 47.

After charging to a desired level, the energy stored in energy storage capacitor 24 may be delivered to patient 16 in the form of a defibrillation pulse. H-bridge 14 is provided to allow the controlled transfer of energy from energy storage capacitor 24 to patient 16. H-bridge 14 is an output circuit that includes four switches 31, 32, 33, and 34, which are driven by four driver circuits 51, 52, 53, and 54, respectively. Each switch is connected in a leg of the output circuit that is arrayed in the form of an "H". Switches 31 and 33 are coupled through a protective component 27 to the positive lead of the energy storage capacitor 24 by a bridge line 26. Protective component 27 limits the current and voltage changes from energy storage capacitor 24, and has both inductive and resistive properties. Switches 32 and 34 are coupled to energy storage capacitor 24 by a bridge line 28.

Patient 16 is connected to the left side of H-bridge 14 by an apex line 17, and to the right side of H-bridge 14 by a sternum line 19. As depicted in FIG. 1, apex line 17 and sternum line 19 are connected to electrodes 15a and 15b, respectively, by a transfer relay circuit 35. Microprocessor 20 is connected to driver circuits 51, 52, 53 and 54 by control lines 42a, 42b, 42c, and 42d, respectively, and to transfer relay circuit 35 by control line 36.

A pace relay 70 and pacer current source 72 are connected in series between apex line 17 and bridge line 28. Pace relay 70 and pacer current source 72 are connected to receive control signals from microprocessor 20 through control lines 42e and 42f, respectively. As will be described in more detail below, pace relay 70 and pacer current source 72 are implemented to generate pacing pulses, and operate in combination with switch 33.

As will be described in more detail below, application of appropriate control signals by microprocessor 20 over the control lines causes switches 31–34 to be appropriately opened and closed and pace relay 70 to be opened, thereby allowing H-bridge 14 to conduct energy from energy storage capacitor 24 to patient 16 in the form of a defibrillation pulse. In a similar manner, microprocessor 20, through appropriate application of the control signals, causes switches 31–34 to be appropriately opened and closed and pace relay 70 to be closed and pacer current source 72 to be activated, thereby allowing H-bridge 14 to conduct energy from storage capacitor 24 to the patient in the form of a monophasic pacing pulse. More specifically, switch 33, which in one embodiment is implemented as an SCR, is activated in combination with the pace relay 70 and the pacer current source 72, in order to generate the pacing pulse. The operation and components of H-bridge output circuit 14 and certain pacing circuits are described in more detail in U.S. Pat. Nos. 6,208,895 and 6,175,765, each of which are commonly assigned and each of which are hereby incorporated by reference in their entireties.

Figure 2:
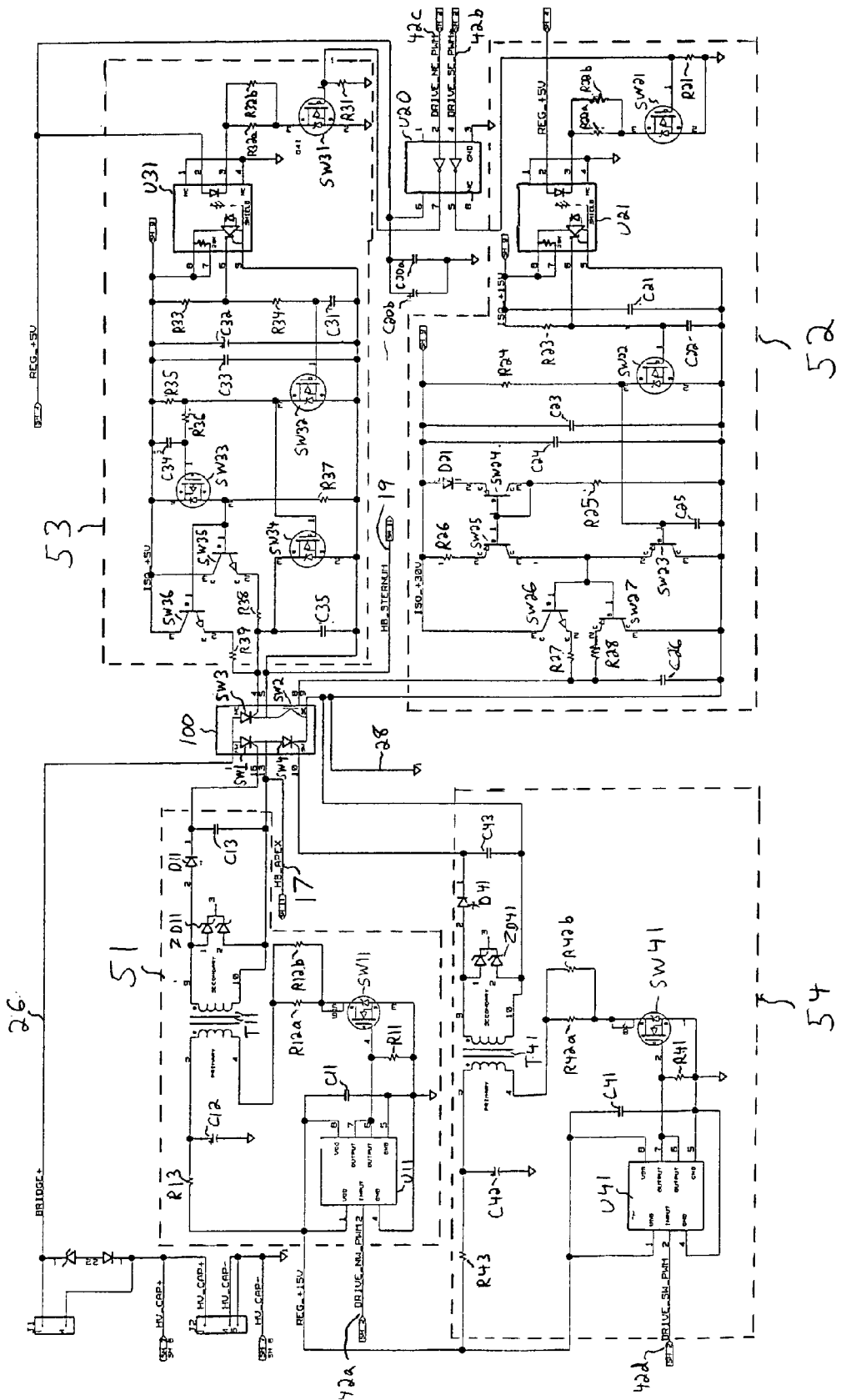
FIG. 2 is a schematic diagram of the H-bridge output circuit of FIG. 1.

A schematic diagram of a preferred construction of H-bridge 14 is shown in FIG. 2. H-bridge 14 uses four output switches SW1–SW4 to conduct energy from energy storage capacitor 24 to patient 16. Switches SW1–SW4 correspond to switches 31–34 of FIG. 1, respectively. Switches SW1, SW3 and SW4 are semiconductor switches, preferably silicon controlled rectifiers (SCRs). Switch SW2 is an insulated gate bipolar transistor (IGBT). Switches SW1–SW4 can be switched from an off (nonconducting) to an on (conducting) condition.

Each of the switches SW1–SW4 is implemented as a single power switch device. Switches SW1–SW4 are packaged in a single surface-mountable package 100 for ease in manufacturing. This circuit package achieves a substantial reduction in overall parts count over previous external defibrillator H-bridges which required multiple switches in each leg, e.g., two or more IGBTs in a leg, and which were not designed to be provided in a single package. The reduction in overall parts count and ease of manufacturing of the single-surface mountable package improves the reliability and manufacturability of the external defibrillator/pacer device 8. In addition, the use of the single IGBT device for a power switch in one of the legs of the H-bridge circuit simplifies the drive circuit requirements for the IGBT over previous H-bridge designs which utilized multiple IGBT devices.

In the defibrillation mode, defibrillator/pacer 8 generates a biphasic defibrillation pulse for application to the patient 16. Initially, switches SW1–SW4 and the pace and transfer relays are opened. Charging of energy storage capacitor 24 is started, and monitored by microprocessor 20 (FIG. 1). When energy storage capacitor 24 is charged to a selected energy level and the transfer relay 35 is closed, switches SW1 and SW2 are switched on so as to connect energy storage capacitor 24 with apex line 17 and sternum line 19 for the application of a first phase of a defibrillation pulse to patient 16. The stored energy travels from the positive terminal of energy storage capacitor 24 on line 26, through switch SW1 and apex line 17, across patient 16, and back through sternum line 19 and switch SW2 to the negative terminal of energy storage capacitor 24 on line 28. The first phase of the biphasic pulse is therefore a positive pulse from the apex to the sternum of patient 16.

Before energy storage capacitor 24 is completely discharged, switch SW2 is biased off to prepare for the application of the second phase of the biphasic pulse. Once switch SW2 is biased off switch SW1 will also become nonconducting, and current through the SCR drops below the holding current for the SCR.

After the end of the first phase of the biphasic defibrillation pulse, switches SW3 and SW4 are switched on to start the second phase of the biphasic pulse. Switches SW3 and SW4 provide a current path to apply a negative defibrillation pulse to patient 16. The energy travels from the positive terminal of energy storage capacitor 24 on line 26, through switch SW3 and sternum line 19, across patient 16, and back through apex line 17 and switch SW4 to the negative terminal of energy storage capacitor 24 on line 28. The polarity of the second phase of the defibrillation pulse is therefore opposite in polarity to the first phase of the biphasic pulse. The end of the second phase of the biphasic pulse is truncated by switching on switch SW1 and switch SW2 to provide a shorted path for the remainder of the capacitor energy through switches SW1 and SW4 and also through switches SW2 and SW3. After energy storage capacitor 24 is discharged, switches SW1–SW4 go to a nonconducting state. Patient isolation relay 35 is then opened. Energy storage capacitor 24 may then be recharged to prepare defibrillator/pacer 8 to apply another defibrillation pulse or to apply pacing pulses.

In the pacing mode, defibrillator/pacer 8 generates a monophasic pacing pulse for application to the patient 16. Initially, switches SW1–SW4 and the pace and transfer relays are opened. Charging of the energy storage capacitor 24 is started, and monitored by the microprocessor 20 (FIG. 1). When the energy storage capacitor 24 is charged to a selected energy level and the transfer relay 35 is closed, the pace relay 70 is closed and the pacer current source 72 and the switch SW3 are switched on so as to connect energy storage capacitor 24 with apex line 17 and sternum line 19 for the application of a pacing pulse to the patient 16. The energy travels from the positive terminal of the energy storage capacitor 24 on line 26, through switch SW3 and sternum line 19, across patient 16, and back through apex line 17 and pace relay 70 and pacer current source 72 to the negative terminal of energy storage capacitor 24 on line 28. The polarity of the pacing pulse is therefore a negative pulse from the apex to the sternum of the patient 16.

As described above, the four output switches SW1–SW4 can be switched from an off (nonconducting) state to an on (conducting) state by application of appropriate control signals on control lines 42a, 42b, 42c, and 42d. In order to allow the SCRs and IGBT to switch the high voltages in an external defibrillator and the low currents for pacer applications, special switch driving circuits 51, 52, 53 and 54 are coupled to switches SW1–SW4, respectively. Control lines 42a, 42b, 42c, and 42d are connected to switch driving circuits 51, 52, 53, and 54, to allow microprocessor 20 to control the state of the switches.

Switch driving circuits 51 and 54 are identical. For purposes of this description, therefore, only the construction and operation of switch driving circuit 51 will be described. Those skilled in the art will recognize that switch driving circuits 51 and 54 operate in a similar manner. Switch driving circuits 51 and 54 are designed to drive the SCR switches SW1 and SW4 so that they are able to both conduct the high-energy defibrillation pulses of 200 or more joules, as well as remaining conducting during low energy defibrillation pulses of at least as low as 1 to 50 joules.

Switch driving circuit 51 includes a control chip U11, a control switch SW11, resistors R11, R12, and R13, capacitors C11, C12, and C13, a diode D11, a component ZD11, and a high-voltage transformer T11. The left side of control chip U11 has pins 1, 2 and 4, while the right side has pins 5, 6, 7 and 8. The left side pins 1, 2 and 4 are for VDD, input, and GND, respectively, while the right side pins 5, 6, 7 and 8 are for VDD, two output pins, and GND, respectively. The input pin 2 is connected to control line 42a. A positive voltage supply REG $V_{15}+$ is coupled to both of the VDD pins 1 and 8. In one embodiment, the positive voltage supply REG $V_{15}+$ is at 15 volts. Ground is connected to both of the GND pins 4 and 5. Both of the output pins 6 and 7 are connected together.

The capacitor C11 is connected between the positive voltage supply REG $V_{15}+$ and ground. The resistor R11 is coupled between the output pin 6 and ground. The gate of the switch SW11 is coupled to the output pin 6, while the source is coupled to ground. The resistors R12a and R12b are coupled in parallel between the drain of the control switch SW11 and the non-dotted end of the primary winding of transformer T11. The capacitor C12 is coupled between the dotted end of the primary winding of the transformer T11 and ground. The resistor R13 is coupled between the dotted end of the primary winding of the transformer T11 and the positive voltage supply REG $V_{15}$+. Resistors R12a, R12b, R13, and capacitor C12 limit and shape the current and voltage waveforms across the primary winding of the transformer T11.

On the secondary winding side of transformer T11, the anode of diode D11 is connected to the dotted end of the secondary winding of transformer T11, and the cathode of diode D11 is coupled to the gate of SCR switch SW1. Capacitor C13 is coupled between the cathode of diode D11 and apex line 17. Apex line 17 is coupled to the non-dotted end of the secondary winding of transformer T11. Component ZD11 is coupled between the dotted and non-dotted ends of the secondary winding of transformer T11. As noted above, the anode of SCR switch SW1 is coupled to the bridge line 26, while the cathode is coupled to apex line 17.

To turn on switch SW1, an oscillating control signal is provided on control line 42a. In this embodiment, the oscillating control signal is a pulse train. The pulse train control signal repeatedly turns control switch SW11 on and off, producing a changing voltage across the primary winding of transformer T11. The voltage is stepped down by transformer T11 and rectified by diode D11 before being applied to the gate of SCR switch SW1. In one embodiment, a 10% duty cycle pulse train on the control line 42a has been found to be adequate to maintain SCR switch SW1 in a conducting state. As long as the control signal is applied to the switch driving circuit 51, the switch SW1 will generally remain in the conducting state. The switch SW1 remains in the conducting state even when conducting relatively low defibrillation currents. In one embodiment, the drive circuits 51 and 54 allow the SCR switches SW1 and SW4 to conduct currents as low as 90 mA. As is well known, once triggered or latched on, an SCR generally remains in the conducting state until the current through the SCR drops below a minimum level (e.g., 90 mA), even if the gate voltage of the SCR is grounded.

IGBT switch SW2 is driven by switch driving circuit 52. Switch driving circuit 52 amplifies the control signal 42b and provides it to the gate of the IGBT switch SW2. It is desirable to drive the IGBT switch SW2 with a high voltage at its gate so that the switch will be able to conduct high currents, as will be described in more detail below. As will also be described in more detail below, it is also desirable to control the turn on and turn off time of the IGBT switch SW2, so as to ensure proper operation of the other switches of the H-bridge 14.

Switch driving circuit 52 includes resistors R21–R28, capacitors C21–C26, switches S21–S27, and an optocoupler U21. Control signal 42b is coupled through an inverter in a component U20 to the switch driving circuit 52. The right side of component U20 has pins 1, 2, 3 and 4, while the right side has pins 5, 6, 7 and 8. The pins 1 and 8 are for NC, while the pin 3 is for GND, and the pin 6 is for VCC. Within the component U20, the pin 2 is coupled through an inverter to the pin 7, while the pin 4 is coupled through another inverter to the pin 5. The GND pin 3 is coupled to ground while the VCC pin 6 is coupled to a positive power supply REG $V_5$+, which in one embodiment may be at +5 volts. Capacitors C20a and C20b are coupled in parallel between pin 6 and ground. As noted above, control signal 42b is coupled to pin 4, which is coupled through an inverter in component U20 to pin 5. Pin 5 is coupled to the input of switch driving circuit 52 at the gate of a control switch SW21.

In switch driving circuit 52, the gate of control switch SW21 is coupled through a resistor R21 to ground, and the source is also coupled to ground. Resistors R22a and R22b are coupled in parallel between the drain of switch S21 and the cathode of an LED which is at a pin 3 of optocoupler U21. On the right side of optocoupler U21 are pins 1–4, which are isolated from pins 5–8 on the left side. The anode of the LED at pin 2 in optocoupler U21 is coupled to the positive voltage supply REG $V_5$+. The two NC pins 1 and 4 are each coupled to ground. Pins 7 and 8 are coupled to the positive voltage power supply ISO $V_{15}$+. Within optocoupler U21, pins 7 and 8 are coupled to one another by a resistor. Pin 6 of optocoupler U21 is coupled by a resistor R23 to the positive voltage supply ISO $V_{15}$+, and to the bridge line 28. Bridge line 28 is referenced as a type of ground potential for the high voltage circuitry of the defibrillator/pacer 8, and is coupled to the negative terminal of the energy storage capacitor 24. Pin 5 is coupled to bridge line 28. A capacitor C21 is coupled between the positive voltage supply ISO $V_{15}$+ and bridge line 28.

Pin 6 of optocoupler U21 is also coupled to the gate of a switch SW22, while the source of switch SW22 is coupled to the bridge line 28. A resistor R24 is coupled between a positive voltage supply ISO $V_{30}$+, and the drain of switch SW22. In one embodiment, the positive voltage supply ISO $V_{30}$+ may be at 30 volts. Capacitors C23 and C24 are coupled in parallel between the positive voltage supply ISO $V_{30}$+ and the bridge line 28. The anode of diode D21 is coupled to the positive voltage supply ISO $V_{30}$+, while the cathode is coupled to the emitter of a switch SW24. The base of switch SW24 is coupled to the base of switch SW25, and is also coupled to the collector of the switch SW24. The collector of switch SW24 is also coupled through a resistor R25 to the bridge line 28. The emitter of switch SW25 is coupled through a resistor R26 to the positive voltage supply ISO $V_{30}$+. The collector of switch SW25 is coupled to the emitter of switch SW23, and also to the bases of switches SW26 and SW27.

The base of switch SW23 is coupled to the drain of switch SW22, and the collector of switch SW23 is coupled to the bridge line 28. The collector of switch SW26 is coupled to the positive voltage supply ISO $V_{30}$+, while the emitter is coupled through a resistor R27 to the gate of IGBT switch SW2. The emitter of switch SW27 is coupled through a resistor R28 to the gate of IGBT switch SW2, while the collector switch SW27 is coupled to the bridge line 28. A capacitor C26 is coupled between the gate of IGBT switch SW2 and the bridge line 28.

It will be appreciated that the optocoupler U21 provides isolation of the high voltage circuitry including IGBT switch SW2, from the low voltage control circuitry including control signal 42b. It will also be appreciated that the switch driving circuit 52 amplifies the control signal 42b for use in driving the gate of the IGBT switch SW2. In one embodiment, the gate of the IGBT switch SW2 may be driven with up to 30 volts, as dictated in part by the positive supply voltage ISO $V_{30}$+.

High currents may sometimes occur in H-bridge 14. One way that high currents may be created is when low resistance is placed between the shock paddles. When this happens, a high current flows between apex line 17 and sternum line 19. In this embodiment, to accommodate high currents without damaging IGBT switch SW2, IGBT switch SW2 may be biased by a high gate voltage (e.g., 30 volts) such that the IGBT can safely conduct upwards of 200 amperes of current.

In one embodiment, the drive circuit 52 is designed so that IGBT switch SW2 is turned on relatively slowly when compared to the fast turn on of SCR switches SW1, SW3, and SW4. A slow turn-on for IGBT switch SW2 is desirable because the IGBT switch is on the same side of H-bridge 14 as SCR switch SW3. SCR switch SW3 is controlled by the control signal on control line 42c, but due to the nature of SCR switches, the SCR switch may be accidentally turned on regardless of the signal on control line 42c if a rapid voltage change occurs across SCR switch SW3. If IGBT switch SW2 was therefore turned on too quickly, the resulting rate of change of the voltage across SCR switch SW3 might cause it to turn on accidentally.

In contrast to the slow turn-on of IGBT switch SW2, the turn-off of the IGBT switch may be performed relatively quickly. The IGBT switch can be quickly turned off because at turn-off there is no concern that the sensitive SCR switches will accidentally turn on.

It will be appreciated that driving circuit 52 allows the IGBT to be used in external defibrillator/pacer 8 where extremely high voltages must be switched in the presence of SCRs. The driving circuit and the use of the single IGBT switch minimizes the number of components required to switch a defibrillation pulse of 200 or more joules. In addition to conducting high currents associated with high-energy defibrillation pulses, the IGBT is also able to conduct very low currents that are associated with defibrillation pulses of as low as 1 to 50 joules.

Switch driving circuit 53 drives SCR switch SW3. As will be described in more detail below, switch driving circuit 53 is designed to be able to drive the SCR for a high current defibrillation pulse, and also maintain the SCR in a conducting state during a low current pacing pulse. The driving circuit 53 is also designed with the desired impedance for driving the SCR switch SW3.

The switch driving circuit 53 includes resistors R31–R39, capacitors C31–C35, switches SW1–SW36, and an optocoupler U31. Optocoupler U31 effectively isolates the high voltage circuitry including SCR switch SW3, from the low voltage control circuitry including control signal 42c. The control signal 42c is coupled through a component U20 to the drive circuit 53. Control signal 42c is coupled to pin 2 of component U20. Within component U20, pin 2 is coupled through an inverter to pin 7, which is coupled to the gate of control switch SW31 of drive circuit 53.

The source of switch SW31 is coupled to ground and the gate is coupled through a resistor R31 to ground. Resistors R32a and R32b are coupled in parallel between the drain of switch SW31 and a pin 3 of optocoupler U31. Optocoupler U31 includes pins 1–4 on the right side, and pins 5–8 on the left side. Pins 1 and 4 are NC pins which are coupled to ground. Within optocoupler U31, pin 3 is coupled to the cathode of an LED and pin 2 is coupled to the anode of the LED. Pin 2 is coupled to the positive voltage supply REG $V_5+$.

Pins 7 and 8 of optocoupler U31 are coupled to a positive voltage supply ISO $V_5+$. Within optocoupler U31, pins 7 and 8 are coupled to one another by a resistor. Pin 5 is coupled to the sternum line 19. Pin 6 is coupled through a resistor R33 to the positive voltage supply ISO $V_5+$. Pin 6 is also coupled through resistor R34 to the gate of switch SW32.

The gate of switch SW32 is also coupled through a capacitor C31 to the sternum line 19. Capacitors C32 and C33 are coupled in parallel between the positive voltage supply ISO $V_5+$ and the sternum line 19. The source of switch SW32 is coupled to the sternum line 19, while the drain is coupled through a resistor R35 to the positive voltage supply ISO $V_5+$. The drain of switch SW32 is coupled to the gate of a switch SW34, and is also coupled through a resistor R36 to the gate of a switch SW33. The gate of switch SW33 is coupled through a capacitor C34 to the positive voltage supply ISO $V_5+$. The drain of switch SW33 is coupled through a resistor R37 to the sternum line 19, and is also coupled to the bases of a switches SW35 and SW36. The source of switch SW33 is coupled to the positive voltage supply ISO $V_5+$.

The source of switch SW34 is coupled to the sternum line 19, while the drain is coupled to the gate of SCR switch SW3. A capacitor C35 is coupled between the gate of SCR switch SW3 and the sternum line 19. The collector of switch SW35 is coupled to the positive voltage supply ISO $V_5+$, while the emitter is coupled through a resistor R38 to the gate of SCR switch SW3. The base of switch SW35 is coupled to the base of switch SW36. The collector of switch SW36 is coupled to the positive voltage supply ISO $V_5+$, while the emitter is coupled through a resistor R39 to the gate of SCR switch SW3.

The operation of drive circuit 53 can be described as follows. When control signal 42c is off, pin 6 of optocoupler U31 goes low, which pulls the gate of switch SW32 low and thus turns off switch SW32. With switch SW32 off, then the gate of switch SW34 is pulled high through the resistor R35, and thus switch SW34 is turned on. With switch SW34 turned on, then the gate of SCR switch SW3 is pulled low, and more specifically, the gate of SCR switch SW3 is shorted to the cathode, thus placing the SCR switch SW3 in a generally nonconducting state.

When control signal 42c is on, pin 6 of optocoupler U31 is pulled high, which causes the gate of switch SW32 to go high. Switch SW32 is thereby turned on, thus causing the gate of switch SW34 to be pulled low, thus turning off switch SW34. With switch SW32 being on, the gate of switch SW33 is pulled low, and since switch SW33 is a P-channel MOSFET, switch SW33 is thereby turned on. This activates switches SW35 and SW36, which provide current amplification and which provide the drive current for the gate of the SCR switch SW3, and thus turns on the SCR switch SW3.

The high driving current for SCR switch SW3 is important for the high energy defibrillation pulses. It is also important for the driving circuit 53 to maintain the SCR switch SW3 in a conducting state for the very low currents which occur during pacing applications. The drive circuit 53 is also designed to match the impedance requirements for driving the SCR switch SW3. In this regard, it should also be noted that when both switches SW35 and SW36 are on, the resistors R38 and R39 are essentially in parallel. In one embodiment, the resistors R38 and R39 may be approximately 21 ohms, so as to produce an overall source impedance of approximately 9 ohms, so as to match the impedance requirements for a particular SCR switch SW3. In other words, the impedance of the drive circuit 53 is selected so as to maintain the load line of the design above the specifications for the SCR switch SW3, so as to ensure that the SCR switch SW3 will remain on in a desired range.

In one embodiment, the defibrillator/pacer 8 is set so that the pacing current is adjustable from 0 to 200 mA, in minimum steps of 10 mA. It should be noted that the drive circuit 53 allows the SCR switch SW3 to remain conducing at these levels, and even at levels far below the 10 mA range. More specifically, the drive circuit 53 provides a relatively high continuous current to the gate of the SCR switch SW3, which in one embodiment may be greater than 100 mA. This high continuous gate to cathode drive current allows the SCR to remain conducting even when the current from the anode to cathode flowing through the SCR switch SW3 is far below the normal holding current for holding on the SCR switch SW3. Thus, for the anode to cathode current, there is essentially no lower limit in practical values for how low of a pacing current could be conducted, since the anode to cathode current required for holding on the SCR is no longer a practical imitation. This is in contrast to previous drive circuits which drove the SCR utilizing driving currents such as a pulse train, for which the SCR switch SW3 might turn off in between the pulses if the anode to cathode current was below the holding current for the SCR. In addition, it should be noted that while a lower drive current such as that used in other SCR driving circuits would conserve more energy, it also would not ensure that the SCR remain conducting for the low current pacing pulses.

Protection for the switches SW1–SW4 is provided in part by protective component 27, which has both inductive and resistive properties. In one embodiment, protective component 27 is implemented with coil of resistance wire that provides an inductive resistance. Protective component 27 limits the rate of change of the voltage across, and current flow to, SCR switches SW1, SW3, and SW4. Too high of a rate of change of the voltage across an SCR switch is undesirable because it can cause the SCR switch to inadvertently turn on. For example, since SCR switches SW1 and SW4 are on the same side of H-bridge 14, any time SCR switch SW4 is abruptly turned on, a rapid voltage change may also result across SCR switch SW1. To prevent rapid voltage changes, protective component 27 reduces the rate of change of the voltage across SCR switch SW1 when SCR switch SW4 is turned on. Also, too high of a current flow can damage the switches SW1, SW3 and SW4, and protective component 27 limits the current flow in H-bridge 14. The use of protective component 27 therefore reduces the need for additional protective components that would otherwise need to be coupled to switches SW1, SW3 and SW4.

It will be appreciated that one advantage of H-bridge 14 described above is that it allows external defibrillator/pacer 8 to generate and apply a high-energy biphasic waveform to a patient. For prior defibrillators providing a monophasic waveform, the standard energy level in the industry for the discharge has been equal to or greater than 200 joules. The above described circuit allows the same amount of energy (approximately equal to or greater than 200 joules) to be delivered to the patient in a biphasic waveform, thereby resulting in a greater certainty of defibrillation effectiveness for a broader range of patients. At the same time, the circuit incorporates special driving circuitry to allow even very low energy biphasic waveforms (e.g., as low as 1 to 50 joules) to be delivered to the patient.

The above described defibrillation mode operation is similar to the operation of the external defibrillator circuit disclosed in previously referenced U.S. Pat. No. 5,873,893. In a manner similar to the defibrillator disclosed in the '893 patent, the present embodiment of the defibrillator/pacer 8 generates a biphasic defibrillation pulse with a positive first phase and a negative second phase (measured from apex line 17 to sternum line 19).

Figure 3:
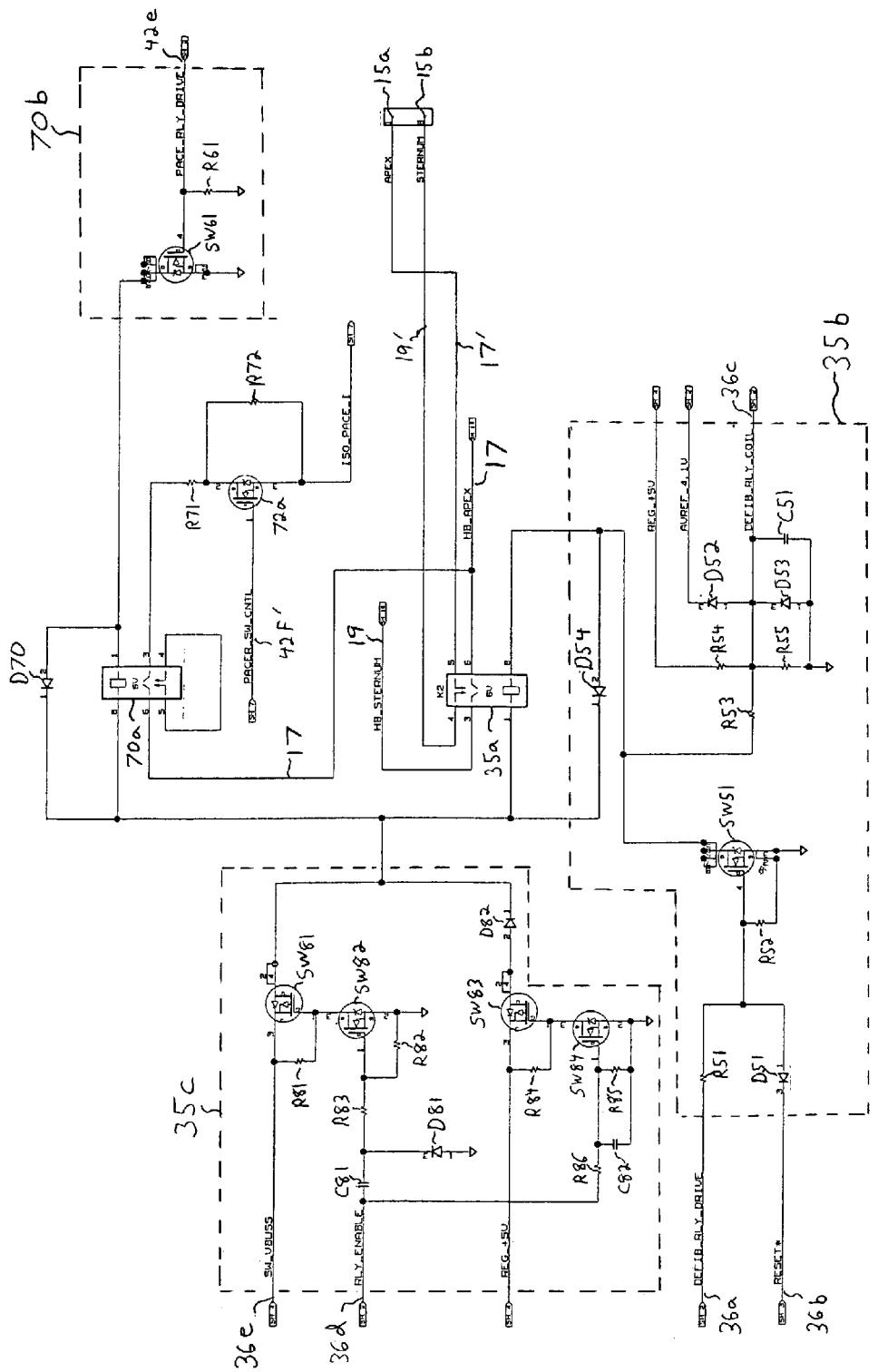
FIG. 3 is a schematic diagram of the transfer and pace relays and the pacer current source of FIG. 1.
Figure 4:
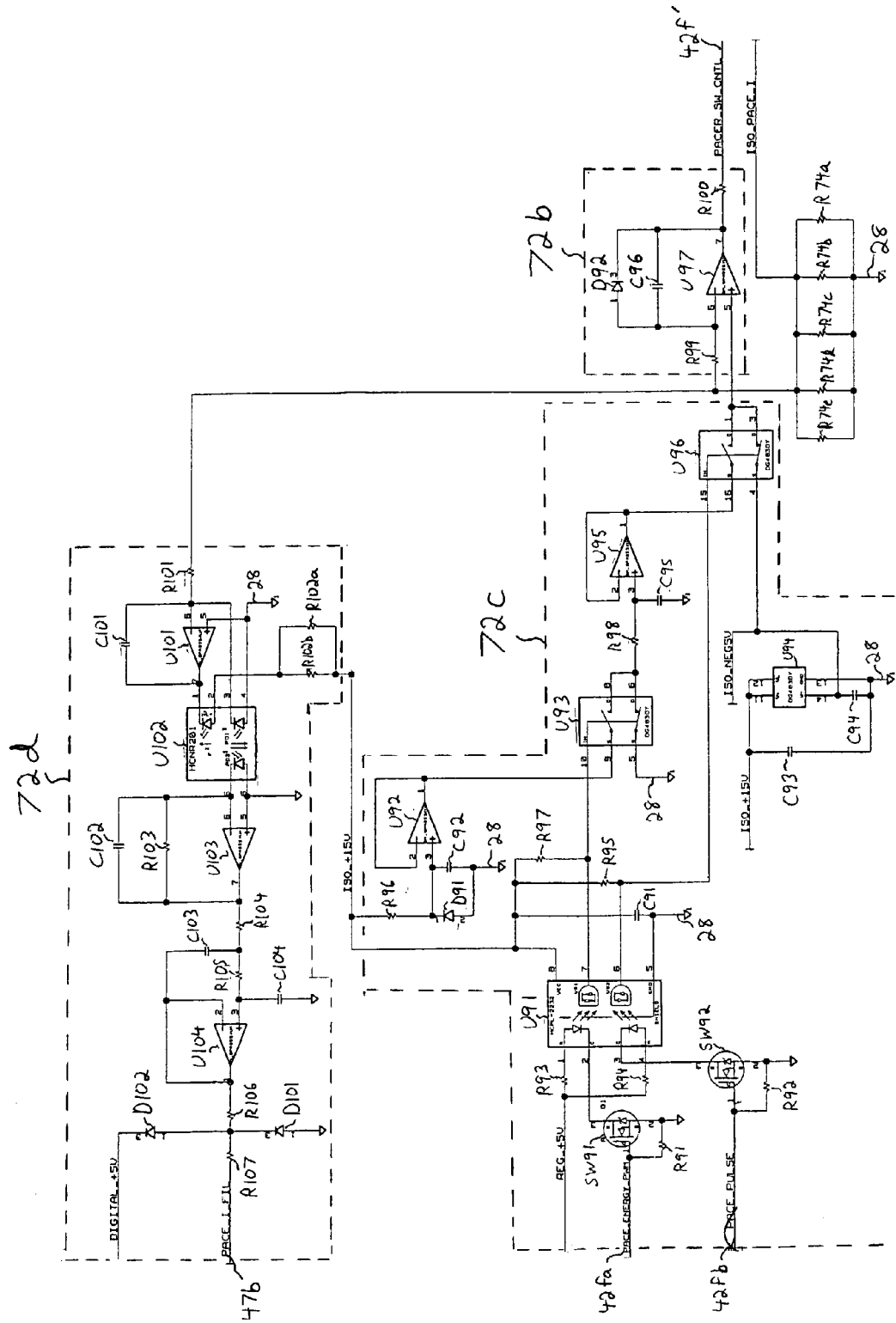
FIG. 4 is a schematic diagram of the control circuitry for the pacer circuitry of FIG. 1.

FIGS. 3 and 4 are schematic diagrams of the transfer relay 35, the pace relay 70, and the pacer current source 72. As shown in FIG. 3, the transfer relay 35 includes a relay 35a which is driven by drive circuits 35b and 35c, which receive the control signals 36a–36e. The pacer relay 70 includes a relay 70a which is driven in part by drive circuits 70b, which receives the control signal 42e. Relay 70a is also driven in part by the same drive circuit 35c which drives relay 35a. The pacer current source 72 includes switch 72a which is driven by drive circuits 72b and 72c, which will be described in more detail below with reference to FIG. 4.

As shown in FIG. 3, relay 35a has pins 1, 3 and 4 on its left side and pins 5, 6, and 8 on its right side. Pin 3 is coupled to sternum line 19, which when the relay is closed is connected to pin 4, which is coupled to a sternum line 19' which may be coupled to electrode 15b. Pin 6 is coupled to apex line 17, which when the relay is closed is connected to pin 5, which is coupled to an apex line 17' which may be coupled to electrode 15a. Pin 1 is coupled to the output of driving circuit 35c, while pin 8 is coupled to the output of driving circuit 35b. The anode of a diode D54 is coupled to pin 8, while the cathode is coupled to pin 1.

Drive circuit 35b includes resistors R51–R54, diodes D51–D54, a capacitor C51, and a control switch SW51. A resistor R51 is coupled between the defibrillator relay drive signal 36a and the gate of control switch SW51. A diode D51 is coupled between a reset signal 36b and the gate of control switch SW51, with the cathode being coupled to the reset signal 36a. Resistor R52 is coupled between the gate and source of control switch SW51. The source of control switch SW51 is coupled to ground, while the drain is coupled to pin 8 of the relay 35a. Resistor R53 is coupled between the drain of control switch SW51 and the anode of diode D52.

Resistor R55, diode D53, and capacitor C51 are coupled in parallel between ground and the anode of diode D52. The anode of diode D52 is coupled to a defibrillator relay coil signal 36c, while the cathode of diode D52 is coupled to a reference voltage AVREF $V_{4.1}$. In one embodiment, the reference voltage AVREF $V_{4.1}$ may be at 4.1 volts. Resistor R54 is coupled between the anode of diode D52 and a positive voltage supply REG $V_5$+. The anode of diode D54 is coupled to pin 8 of the relay 35a, while the cathode is coupled to pin 1.

Relay drive circuit 35c includes resistors R81–R86, diodes D81 and D82, capacitors C81 and C82, and switches SW81–SW84. The source of switch SW81 is coupled to a SW VBUSS signal 36e. The gate of switch SW81 is coupled through a resistor R81 to the source of switch SW81. The drain of switch SW81 is coupled to pin 1 of transfer relay 35a, and to pin 8 of pace relay 70a. The gate of switch SW81 is coupled to the drain of switch SW82.

The source of switch SW82 is coupled by resistor R82 to the gate of switch SW82. The gate of switch SW82 is coupled through a resistor R83 to the cathode of diode D81. The anode of diode D81 is coupled to ground. A capacitor C81 is coupled between the cathode of diode D81 and a relay enable signal 36d.

The relay enable signal 36d is also coupled to a resistor R86 through the gate of switch SW84. Capacitor C82 and resistor R85 are coupled in parallel between the gate of switch SW84 and the source of switch SW84. The source of switch SW84 is coupled to ground. The drain of switch SW84 is coupled to the gate of switch SW83. A resistor R84 is coupled between the source of switch SW83 and the gate of switch SW83. A positive voltage supply REG $V_5$+ is coupled to the source of switch SW83. The anode of diode D82 is coupled to the drain of switch SW83, while the cathode is coupled to pin 1 of transfer relay 35a and pin 8 of pace relay 70a.

Transfer relay 35 is operated such that when the defibrillator 8 is to apply a defibrillation pulse or a pacing pulse to the patient 16, the relay is closed. When the relay is open, it isolates the patient 16 from the rest of the defibrillator/pacer 8 circuitry. As described above, the transfer relay includes drive circuits 35b and 35c which drive the relay 35a. The drive circuit 35c is coupled to the high side switch that is common for each coil in each of the relays 35a and 70a. The drive circuit 35c provides increased driving for the relays in order to allow them to be turned on quickly.

Pace relay 70 includes relay 70a which is driven by drive circuits 70b and 35c. Relay 70a has pins 1, 3, and 4 on its right side, and pins 5, 6, and 8 on its left side. A diode D70 is coupled between coil pins 1 and 8, with the anode coupled to pin 1. As described above, pin 8 is coupled to the output of drive circuit 35c. Pins 5 and 4 are shorted together, while pin 6 is coupled to apex line 17. When the relay 70a is closed, pin 6 is coupled to pin 5, and pin 4 is coupled to pin 3. Pin 1 is coupled to the output of drive circuit 70b which includes a switch SW61 and a resistor R61. The gate of switch SW61 is coupled to the pace relay drive signal 42e. Resistor R61 is coupled between the gate of switch SW61 and ground. The source of switch SW61 is coupled to ground. The drain of switch SW61 is coupled to pin 1 of relay 70a.

Pin 3 of relay 70a is coupled through a resistor R71 to the drain of pacer current source switch 72a. The drain of switch 72a is coupled to the source by a resistor R72. The source of switch 72a is coupled through a sense resistor R74 to bridge line 28, as will be described in more detail below with reference to FIG. 4. The gate of switch 72a is coupled to a pacer SW CNTL signal 42f. The control signal 42f comes from driver circuits 72b and 72c, which will be described in more detail below with reference to FIG. 4.

As shown in FIG. 4, driver circuit 72b includes resistors R99 and R100, capacitor C96, diode D92, and an operational amplifier U97. Operational amplifier U97 is coupled in a feedback loop configuration with switch 72a as part of an adjustable pacer current source. Diode D92 and capacitor C96 are coupled in parallel between the negative input of operational amplifier U97 and the output of operational amplifier U97. Resistor R100 is coupled between the output of operational amplifier U97 and control signal 42f. Resistor R99 is coupled between the negative input of operational amplifier U97 and the source of switch 72a (FIG. 3). Resistor 74 comprises resistors R74a–R74e which are coupled in parallel between bridge line 28 and the source of the pacer current source switch 72a.

Driver circuit 72b receives control signals from driver circuit 72c. As will be described in more detail below, driver circuit 72c receives control signals 42f from the microprocessor 20, converts the signals to transfer them across the isolation barrier, and then reconverts the signals to control the feedback loop of driver circuit 72b.

Driver circuit 72c includes resistors R91–R98, switches SW91–SW92, capacitors C91–C95, and components U91–U96. Optocoupler U91 includes pins 1–4 on the left side and pins 5–8 on the right side. Within optocoupler U91, pin 1 is coupled to pin 2 by an LED which is sensed at pin 7, and pin 4 is coupled to pin 3 by an LED which is sensed at pin 6. GND pin 5 is coupled to bridge line 28, while VCC pin 8 is coupled to a positive voltage supply ISO $V_{15}+$.

Pin 1 of optocoupler U91 is coupled through a resistor R93 to a positive voltage supply REG $V_5+$. Pin 4 is coupled through a resistor R94 to the positive voltage supply REG $V_5+$. Pin 2 is coupled to the drain of switch SW91, while pin 3 is coupled to the drain of switch SW92. The gate of switch SW91 is coupled by a resistor R91 to the source of switch SW91, while the gate of switch SW92 is coupled by a resistor R92 to the source of switch SW92. Both of the sources of switches SW91 and SW92 are coupled to ground. The gate of switch SW91 receives a pace energy PWM signal 42fa, while the gate switch SW92 receives a pace pulse signal 42fb. A capacitor C91 is coupled between pins 5 and 8 of optocoupler U91. Resistor R5 is coupled between pins 6 and 8, while resistor R7 is coupled between pins 7 and 8.

An operational amplifier U92 is coupled to serve as a buffer and essentially provides a 5-volt reference. The negative input of operational amplifier U92 is coupled to its output. A diode D92 and capacitor C92 are coupled in parallel between the positive input of the operational amplifier U92 and the bridge line 28. Resistor R96 is coupled between the positive input at the operational amplifier U92 and the positive voltage source ISO $V_{15}+$.

The switching component U93 includes pins 5, 9 and 10 on its left side and pins 6 and 8 on its right side. Within switching component U93, pin 10 is coupled to a control signal, while pin 9 is coupled to pin 8 by a first switch and pin 5 is coupled to pin 6 by a second switch. Pin 5 is coupled to bridge line 28. Pin 9 is coupled to the output of operational amplifier U92. Pin 10 is coupled to output pin 7 of optocoupler U91. Pin 8 of switching component U93 is shorted to pin 6. A resistor R98 is coupled between pin 6 and the positive input of an operational amplifier U95.

A capacitor C95 is coupled between the positive input of operational amplifier U95 and bridge line 28. The negative input of operational amplifier U95 is coupled to the output of operational amplifier U95. The output of operational amplifier U95 is coupled to a pin 16 of a switching component U96.

Switching component U96 includes pins 15, 16 and 4 on its left side, and pins 1 and 3 on its right side. Within switching component U96, pin 15 is coupled to a control signal, while pin 16 is coupled to pin 1 by a first switch, and pin 4 is coupled to pin 3 by a second switch. Pin 5 is coupled to output pin 6 of optocoupler U91. Pin 4 is coupled to a negative voltage supply ISO $V_5-$. Pins 1 and 3 of switching component U96 are shorted together, and are also coupled to the positive input of operational amplifier U97.

Capacitor C93 is coupled between the positive voltage supply ISO $V_{15}+$ and the bridge line 28. Capacitor C94 is coupled between the negative voltage supply ISO $V_5-$ and the bridge line 28. Component U94 has four pins 11–14, with pins 11 and 12 being coupled to positive voltage supply ISO V1$_5+$, pin 13 being coupled to bridge line 28, and pin 14 being coupled to the negative voltage supply ISO $V_5-$.

As will be described in more detail below, driver circuit 72b utilizes operational amplifier U97 in a conventional feedback loop as part of the pacer current source 72. Driver circuit 72c receives the analog control signal from the microprocessor, transfers it across the isolation barrier, then converts the signal back to a DC control signal. The signals from the microprocessor 20 (FIG. 1) are pulse width modulated (PWM) signals. Pin 7 of optocoupler U91 provides a duty cycle modulated output, and switching component U96 toggles between a negative 5 volt signal and the output of operational amplifier U95. Operational amplifier U95 includes a resistor capacitor filter which converts the pulse width modulated signal into a DC signal proportional to the duty cycle. The input of the operational amplifier U95 is received from the switching component U93 which is controlled by the pin 7 of optocoupler U91, as described above. The end result is that the control signals 42fa and 42fb from the microprocessor are converted into a DC signal proportional to the duty cycle, which determines the pacer current of the pacer current source 72a of FIG. 3. In other words, the microprocessor is able to control the pacer current in accordance with control signals 42fa and 42fb.

Pacer current source 72 also includes a monitor circuit 72d and a sense resistor 74 which provide the microprocessor 20 with feedback as to the operation of the pacer current source 72. Monitor circuit 72d monitors the voltage on sense resistor R74, which indicates the level of pacer current. As will de described in more detail below, monitor circuit 72d is utilized by the microprocessor 20 to monitor the pacer current to ensure that the control signal 42f is controlling the pacer current properly, and that when a pacing control signal is sent that a pacing pulse is generated.

Monitor circuit 72d includes resistors R101–R107, capacitors C101–C104, diodes D101–D102, and components U101–U104. Resistor R101 is coupled between resistor R74 and the negative input of an operational amplifier U101. A capacitor C101 is coupled between the negative input of operational amplifier U101 and the output of operational amplifier U101. The positive input of operational amplifier U101 is coupled to bridge line 28. The output of operational amplifier U101 is coupled to a pin 1 of an optocoupler U102.

Optocoupler U102 includes pins 1–4 on its right side, and pins 5 and 6 on its left side. Within the optocoupler, pin 2 is coupled to pin 1 by an LED, while pin 4 is coupled to pin 3 by a sensor, and pin 5 is coupled to pin 6 by a sensor. Resistors R102a and R102b are coupled in parallel between pin 2 and positive voltage supply ISO $V_{15}$+. Pin 4 is coupled to bridge line 28, and pin 3 is coupled to the negative input of operational amplifier U101. Pin 5 is coupled to ground and pin 6 is coupled to the negative input of an operational amplifier U103.

A capacitor C102 and a resistor R103 are coupled in parallel between the negative input of operational amplifier U103 and the output of operational amplifier U103. A resistor 104 and a resistor 105 are coupled in series between the output of operational amplifier U103 and the positive input of an operational amplifier U104. A capacitor C103 is coupled between the node between resistors R104 and R105, and the negative input of operational amplifier U104. A capacitor C104 is coupled between the positive input of operational amplifier U104 and ground. The negative input of operational amplifier U104 is coupled to the output of operational amplifier U104.

Resistor R106 is coupled between the output of operational amplifier U104 and the cathode of a diode D101. Diode D101 is coupled between ground and the anode of a diode D102. Diode D102 is coupled between the cathode of diode D101 and the positive voltage supply DIGITAL $V_5$+. A resistor R107 is coupled between the cathode of diode D101 and the output sensor signal 47b.

As described above, the monitor circuit 72d provides the output sensor signal 47b to the microprocessor 20. More specifically, when current from the pacer current source switch 72a flows through sense resistor R74, the voltage at sense resistor 74 is provided to the monitor circuit 72d. The monitor circuit 72d then provides the output signal 47b which indicates the sensed voltage, and thus indicates the current that is flowing through the pacer current source 72.

The overall operation of the pacer current source 72, including switch 72a and circuits 72b, 72c, and 72d, can be described as follows. Switch driving circuit 72b uses a feedback scheme to control switch 72a to achieve a desired output current. Microprocessor 20 monitors the current output by switch 72a through resistor R74 and sensor circuit 72d as previously described and adjusts the voltage level of the control signal at control lines 42f to achieve the desired current level. Capacitor C96 causes switch driving circuit 72a to function in a manner similar to an integrator, with its input signal being the voltage at the source of switch 72a. Thus, when the signal at control line 42f dictates a zero voltage, the output voltage of operational amplifier U97 is zero, causing switch 72a to be non-conductive.

When the voltage dictated by control lines 42f through circuit 72a is positive relative to the voltage at the inverting input lead of operational amplifier U97, the "integrator" operates to increase the voltage at its output lead, which in turn causes switch 72a to be more conductive and pull up the voltage at its source. Because this source voltage is fed back to the inverting input lead of operational amplifier U97, the "integrator" only increases its output voltage until the source voltage is substantially equal to the voltage at the non-inverting input lead. That is, the "virtual ground" effect of operational amplifiers causes the "integrator" to quickly drive the source voltage to be equal to the voltage dictated by control lines 42f.

In a symmetrically opposite manner, when the voltage dictated by control lines 42f is negative relative to the voltage at the inverting input lead of operational amplifier U97, the "integrator" operates to decrease the voltage at its output lead, which in turn causes switch 72a to become less conductive and quickly drive the source voltage of switch 72a to be substantially equal to the voltage dictated by control lines 42f. Diode D92 helps to prevent the voltage at the source of switch 72a from being above the voltage at the gate of switch 72a by more than a diode threshold voltage.

Thus, when the microprocessor 20 wishes to increase the output current of pacer current source switch 72a, the microprocessor 20 increases the signal at control lines 42f. As described above, increasing the signal at control lines 42f causes the output current of switch 72a to increase, which is then detected by the microprocessor in monitoring the voltage across resistor R74 through the sensor circuit 72d. When the output current reaches the desired level, microprocessor 20 can then stop increasing the signal at control lines 42f. Conversely, to decrease the output current of switch 72a, microprocessor 20 causes the signal at control lines 42f to decrease, thereby causing the output current of switch 72a to decrease. When the output current reaches the desired level, microprocessor 20 can then stop decreasing the signal at control lines 42f.

The overall operation of the pace relay 70 in combination with the pacer current source 72 can be described as follows. When conductive, pace relay 70 and pacer current source 72 provide a current path from apex line 17 to bridge line 28. As described above, pace relay 70 includes a relay 70a and a driver circuit 70b, while pacer current source 72 includes a switch 72a and driver circuits 72b and 72c. Relay 70a and switch 72a are turned off and on by driving circuits 70b, and 72b and 72c, in response to control signals from microprocessor 20, which are received on control lines 42e and 42f, respectively. In addition, in this embodiment, microprocessor 20 is connected to monitor the voltage across resistor R74 via monitor circuit 72d during the pacing mode. Microprocessor 20 is configured to provide the control signal over control lines 42f to cause switch driving circuit 72b to operate switch 72a so that the current conducted by switch 72a can be adjusted to a desired level. In one embodiment, the technique used is referred to as a constant current pacing technique, in that the current can be maintained at a constant peak level even if patient impedance changes between pulses and is not adjusted with regard to the energy discharged by energy storage capacitor 24.

In the pacing mode, pace relay 70, pacer current source 72, and switch SW3 are turned on. Pacer current source 72 is controlled by microprocessor 20 (FIG. 1) to provide a desired level of pacing current to apex line 19. In one embodiment, the pacing current is typically increased by about 5 mA with each successive pacing pulse until the pulses are of sufficient strength to cause the heart muscle to contract. Microprocessor 20 controls switch SW3 to be turned on for the desired duration of a pacing pulse. As described above, driver circuit 53 is specially designed to maintain SCR switch SW3 in a conducting state even for the relatively small currents of the pacing pulses.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A circuit for use in an external unit that generates a defibrillation pulse in a defibrillation mode and a pacing pulse in a pacing mode, the circuit comprising:
    at least one energy storage device having a first electrode and a second electrode; a charging circuit coupled to the energy storage device, wherein the charging circuit is configured to charge the energy storage device;
    an energy transfer circuit coupled to the energy storage device, the energy transfer circuit having a first output lead and a second output lead, and also having a plurality of output switches including one or more SCR switches in an H-bridge circuit having a first leg, a second leg, a third leg, and a fourth leg, wherein the energy transfer circuit is configured to switch the plurality of output switches to selectively electrically couple the first and second electrodes of the energy storage device to the first and second output leads; and
    a control circuit coupled to the charging circuit and the energy transfer circuit, wherein the control circuit is configured to control the energy transfer circuit to couple the first and second electrodes of the energy storage device to the first and second output leads of the energy transfer circuit such that:
        during the defibrillation mode, a defibrillation pulse is conducted at least in part through at least one SCR switch and at least two H-bridge circuit legs of the energy transfer circuit to the first and second output leads, and
        during the pacing mode, a pacing pulse is conducted through the same at least one SCR switch and only one H-bridge circuit leg of the energy transfer circuit to the first and second output leads.

2. The circuit of claim 1, wherein the control circuit includes a gate drive circuit for driving the gate of the at least one SCR switch with a gate drive signal.

3. The circuit of claim 2, wherein the gate drive signal supplied by the gate drive circuit biases the at least one SCR switch in a conducting state, the SCR switch remaining biased in the conducting state as long as the gate drive signal is present and as long as the current through the SCR is above a minimum level.

4. The circuit of claim 3, wherein the level of current required for pacing pulses is above the minimum current level required to keep the at least one SCR switch in the conducting state while the gate drive circuit is driving the gate of the SCR switch.

5. The circuit of claim 4, wherein the gate drive circuit also drives the gate of the at least one SCR with sufficient voltage so as to allow the SCR to conduct external defibrillation pulses.

6. The circuit of claim 5, wherein the plurality of output switches comprise at least a second SCR switch and a second drive circuit for the second SCR switch, the second drive circuit driving the second SCR switch with sufficient voltage so as to allow the second SCR switch to conduct high energy external defibrillation pulses, but the second drive circuit also being different from the first drive circuit in that it does not drive the second SCR switch so that it would remain conducting at the level of current required for some pacing pulses.

7. The circuit of claim 5, wherein the H-bridge output circuit and the plurality of output switches comprise:
    (a) a first switch in the first leg of the H-bridge output circuit coupled between a first lead of the at least one energy storage device and the first electrode;
    (b) a second switch in the second leg of the H-bridge output circuit coupled between a second lead of the at least one energy storage device and the second electrode;
    (c) a third switch in the third leg of the H-bridge output circuit coupled between the first lead of the at least one energy storage device and the second electrode; and
    (d) a fourth switch in the fourth leg of the H-bridge output circuit coupled between the second lead of the at least one energy storage device and the first electrode.

8. The circuit of claim 7, wherein the at least one energy storage device comprises one or more energy storage capacitors.

9. The circuit of claim 7, further comprising a protective component coupled between the at least one energy storage device and the output circuit, the protective component having both inductive and resistive properties so as to limit the current to, and a rise time of the voltage across, the at least one output circuit.

10. The circuit of claim 7, wherein each of the first, third, and fourth switches comprise an SCR switch.

11. The circuit of claim 10, wherein the third switch is the at least one SCR switch that conducts pacing pulses during the pacing mode.

12. The circuit of claim 11, wherein the control circuit includes a plurality of gate drive circuits, each of the plurality of gate drive circuits coupled to the gate of one of each of the SCR switches.

13. The circuit of claim 12, wherein the gate drive circuits for the first and fourth switches produce a pulse train and supply said pulse train to the gate of the first and fourth SCR switches as a gate signal.

14. The circuit of claim 13, wherein the drive circuit for the third SCR switch does not produce a pulse train.

15. The circuit of claim 7, wherein the second switch comprises a single IGBT switch, the IGBT having a gate, a collector, and an emitter, the gate being connected for receiving gate signals, the collector and emitter being connected in a circuit path to provide current through the IGBT.

16. The circuit of claim 15, wherein the control circuit includes a gate drive circuit coupled to the gate of the IGBT, the gate drive circuit providing a gate signal to the gate of the IGBT for switching the IGBT between a conducting state and a nonconducting state.

17. The circuit of claim 16, wherein the gate drive circuit supplies a gate signal that maintains the IGBT in a saturated state when the IGBT is in the conducting state.

18. The circuit of claim 7, wherein the H-bridge circuit comprises a current source circuit, the current source circuit being coupled in parallel with one of the legs of the energy transfer circuit, and wherein the current source circuit is configured to provide a configurable current to the output leads during the pacing mode and is configured to provide essentially no current to the output leads during the defibrillation mode.

19. The circuit of claim 18, wherein during the pacing mode, the control circuit is configured to cause the current source circuit to provide the configurable current with a predetermined current level.

20. The circuit of claim 7, wherein the four legs of the H-bridge output circuit each comprise a singe output switch, and all four of the H-bridge output switches are contained within a single surface mountable package.

21. The circuit of claim 1, wherein the output switches are driven so that they are capable of conducting a least approximately 200 amperes of current.

22. The circuit of claim 1, wherein the output switches are driven so that they are capable of conducting defibrillation pulses of as high as 200 or more joules and as low as 50 or less joules.

23. The circuit of claim 1, wherein the output switches are driven so that they are capable of conducting external defibrillation pulses of as low as 1 joule or less.

24. The circuit of claim 1, wherein the control circuit includes a gate drive circuit for driving the gate of the at least one SCR switch with a gate drive signal so that the at least one SCR remains conducting for pacing currents as low as approximately 10 mA.

25. The circuit of claim 24, wherein the gate drive signal comprises a continuous drive current to the gate of the SCR switch.

26. The circuit of claim 25, wherein the continuous drive current is at least approximately 100 mA.

27. A method of externally providing a defibrillation pulse or a pacing pulse to a patient from a single unit that includes one or more SCR switches, the method comprising:
 charging an energy storage capacitor;
 during a defibrillation mode, transferring energy from the energy storage capacitor through a first SCR switch and at least two legs of an H-bridge circuit to the patient in a defibrillation pulse; and
 during a pacing mode, transferring energy from the energy storage capacitor through the first SCR switch and only one leg of the H-bridge circuit to the patient in a pacing pulse.

28. The method of claim 27, wherein an energy transfer circuit is used to transfer energy from the energy storage capacitor to the patient in both the defibrillation and pacing modes.

29. In an external defibrillator for applying a multiphasic defibrillation pulse to a patient through first and second electrodes when said first and second electrodes are coupled to a patient, said external defibrillator including one or more energy storage devices having first and second leads and a charging system for charging said one or more energy storage devices, said external defibrillator also including one or more output circuits with a plurality of output switches for switchably coupling the one or more energy storage devices to the first and second electrodes in order to conduct the energy stored in the one or more energy storage devices to a patient, said output switches including one or more SCR switches coupled in an H-bridge circuit, said external defibrillator further comprising a control circuit coupled to said plurality of output switches for controlling said output circuit switches, said control circuit switching the plurality of output switches so as to generate a multiphasic defibrillation pulse for application to a patient via at least two legs of the H-bridge circuit, the improvement comprising:
 configuring one or more of said SCR switches in only one leg of the H-bridge circuit of said output circuit to also conduct pacing pulses to a patient, such that said one or more SCR switches are utilized to conduct both defibrillation and pacing pulses.

* * * * *